(12) United States Patent
Romer et al.

(10) Patent No.: US 11,255,190 B2
(45) Date of Patent: Feb. 22, 2022

(54) HYDROCARBON WELLS AND METHODS OF INTERROGATING FLUID FLOW WITHIN HYDROCARBON WELLS

(71) Applicant: ExxonMobil Upstream Research Company, Spring, TX (US)

(72) Inventors: Michael C. Romer, The Woodlands, TX (US); Ted A. Long, Spring, TX (US); Tony W. Hord, Spring, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 66 days.

(21) Appl. No.: 16/846,961

(22) Filed: Apr. 13, 2020

(65) Prior Publication Data

US 2020/0362698 A1    Nov. 19, 2020

Related U.S. Application Data

(60) Provisional application No. 62/849,230, filed on May 17, 2019.

(51) Int. Cl.
*E21B 49/08* (2006.01)
*E21B 43/12* (2006.01)
(Continued)

(52) U.S. Cl.
CPC ........ *E21B 49/0875* (2020.05); *E21B 43/123* (2013.01); *E21B 47/01* (2013.01); *E21B 47/06* (2013.01); *E21B 47/07* (2020.05); *E21B 47/10* (2013.01); *G01N 33/2823* (2013.01); *G01V 9/005* (2013.01); *G01V 11/002* (2013.01)

(58) Field of Classification Search
CPC .... E21B 49/0875; E21B 43/123; E21B 47/06; E21B 47/07; E21B 47/10; E21B 47/01; G01N 33/2823; G01V 9/005; G01V 11/002; G01V 3/20
See application file for complete search history.

(56) References Cited

U.S. PATENT DOCUMENTS

| 5,031,697 A * | 7/1991 | Wellington | ............ E21B 43/122 |
| | | | 166/250.12 |
| 6,989,764 B2 | 1/2006 | Thomeer et al. | |

(Continued)

*Primary Examiner* — Giovanna Wright
*Assistant Examiner* — Yanick A Akaragwe
(74) *Attorney, Agent, or Firm* — Leandro Arechederra, III

(57) ABSTRACT

Hydrocarbon wells and methods of interrogating fluid flow within hydrocarbon wells. The hydrocarbon wells include a wellbore and downhole tubing that defines a tubing conduit and extends within the wellbore. The hydrocarbon wells also include an interrogation device. The interrogation device is configured to indicate at least one property of fluid flow within the hydrocarbon wells. The hydrocarbon wells also include a downhole location at which the interrogation device is released into the tubing conduit and a detection structure configured to query the interrogation device to determine the at least one property of fluid flow within the hydrocarbon wells. The methods include releasing an interrogation device at a downhole location within a hydrocarbon well and flowing the interrogation device from the downhole location to a surface region. The methods also include querying the interrogation device to determine at least one property of fluid flow within the hydrocarbon well.

17 Claims, 3 Drawing Sheets

(51) Int. Cl.
      *E21B 47/06*       (2012.01)
      *E21B 47/07*       (2012.01)
      *G01N 33/28*       (2006.01)
      *E21B 47/10*       (2012.01)
      *G01V 9/00*        (2006.01)
      *G01V 11/00*       (2006.01)
      *E21B 47/01*       (2012.01)

(56) References Cited

U.S. PATENT DOCUMENTS

| | | |
|---|---|---|
| 9,109,424 B2 | 8/2015 | Jeffries et al. |
| 9,447,677 B2 | 9/2016 | Fielder et al. |
| 2003/0056952 A1* | 3/2003 | Stegemeier ............. E21B 47/11 166/250.12 |
| 2010/0198533 A1* | 8/2010 | Peacock ................ E21B 43/122 702/47 |
| 2014/0260588 A1 | 9/2014 | Jaaskelainen et al. |
| 2014/0305636 A1 | 10/2014 | Paulet et al. |
| 2016/0041132 A1 | 2/2016 | Romer et al. |
| 2016/0222779 A1* | 8/2016 | Peters ..................... E21B 47/11 |
| 2017/0255210 A1* | 9/2017 | Wu ......................... F15B 1/265 |
| 2018/0051700 A1 | 2/2018 | Sheth et al. |
| 2021/0040813 A1* | 2/2021 | Inyang .................... E21B 47/10 |

\* cited by examiner

HYDROCARBON WELLS AND METHODS OF INTERROGATING FLUID FLOW WITHIN HYDROCARBON WELLS

CROSS-REFERENCE TO RELATED APPLICATION

This application claims the benefit of U.S. Provisional Application 62/849,230 filed May 17, 2019 entitled HYDROCARBON WELLS AND METHODS OF INTERROGATING FLUID FLOW WITHIN HYDROCARBON WELLS, the entirety of which is incorporated by reference herein.

FIELD OF THE DISCLOSURE

The present disclosure relates generally to hydrocarbon wells and methods of interrogating fluid flow within hydrocarbon wells, and more particularly to hydrocarbon wells and methods that utilize an interrogation device to indicate and/or determine at least one property of fluid flow within the hydrocarbon well.

BACKGROUND OF THE DISCLOSURE

It may be desirable to more fully understand downhole conditions within a hydrocarbon well. As examples, general knowledge of fluid flows, temperatures, pressures, pH, and the like, within the hydrocarbon well, may be utilized to more effectively develop hydrocarbon reserves and/or to optimize production from the hydrocarbon well. In the context of gas lift operations, knowledge of which gas lift valve(s) are providing lift at a given point in time may be beneficial. Such information may be utilized to optimize gas lift operations and/or to indicate when individual gas lift valves are in need of calibration, repair, and/or replacement.

Historically, tracer injection has been utilized to characterize fluid flows within a hydrocarbon well. While tracer injection sometimes can be effective, it is costly and time-consuming to implement. In addition, there generally is a significant amount of uncertainty associated with the obtained results. Thus, there exists a need for improved hydrocarbon wells and/or for improved methods of interrogating fluid flow within hydrocarbon wells.

SUMMARY OF THE DISCLOSURE

Hydrocarbon wells and methods of interrogating fluid flow within hydrocarbon wells. The hydrocarbon wells include a wellbore that extends between a surface region and a subterranean formation and downhole tubing that defines a tubing conduit and extends within the wellbore. The hydrocarbon wells also include an interrogation device. The interrogation device is configured to indicate at least one property of fluid flow within the hydrocarbon wells. The hydrocarbon wells also include a downhole location at which the interrogation device is released into the tubing or fluid-flowing conduit and a detection structure configured to query the interrogation device to determine the at least one property of fluid flow within the hydrocarbon wells.

The methods include releasing an interrogation device at a downhole location within a hydrocarbon well and flowing the interrogation device from the downhole location to a surface region. The flowing is via a tubing conduit that is defined by downhole tubing. The downhole tubing extends within a wellbore of the hydrocarbon well. The methods also include querying the interrogation device to determine at least one property of fluid flow within the hydrocarbon well.

DETAILED DESCRIPTION AND BEST MODE OF THE DISCLOSURE

Figure 1:
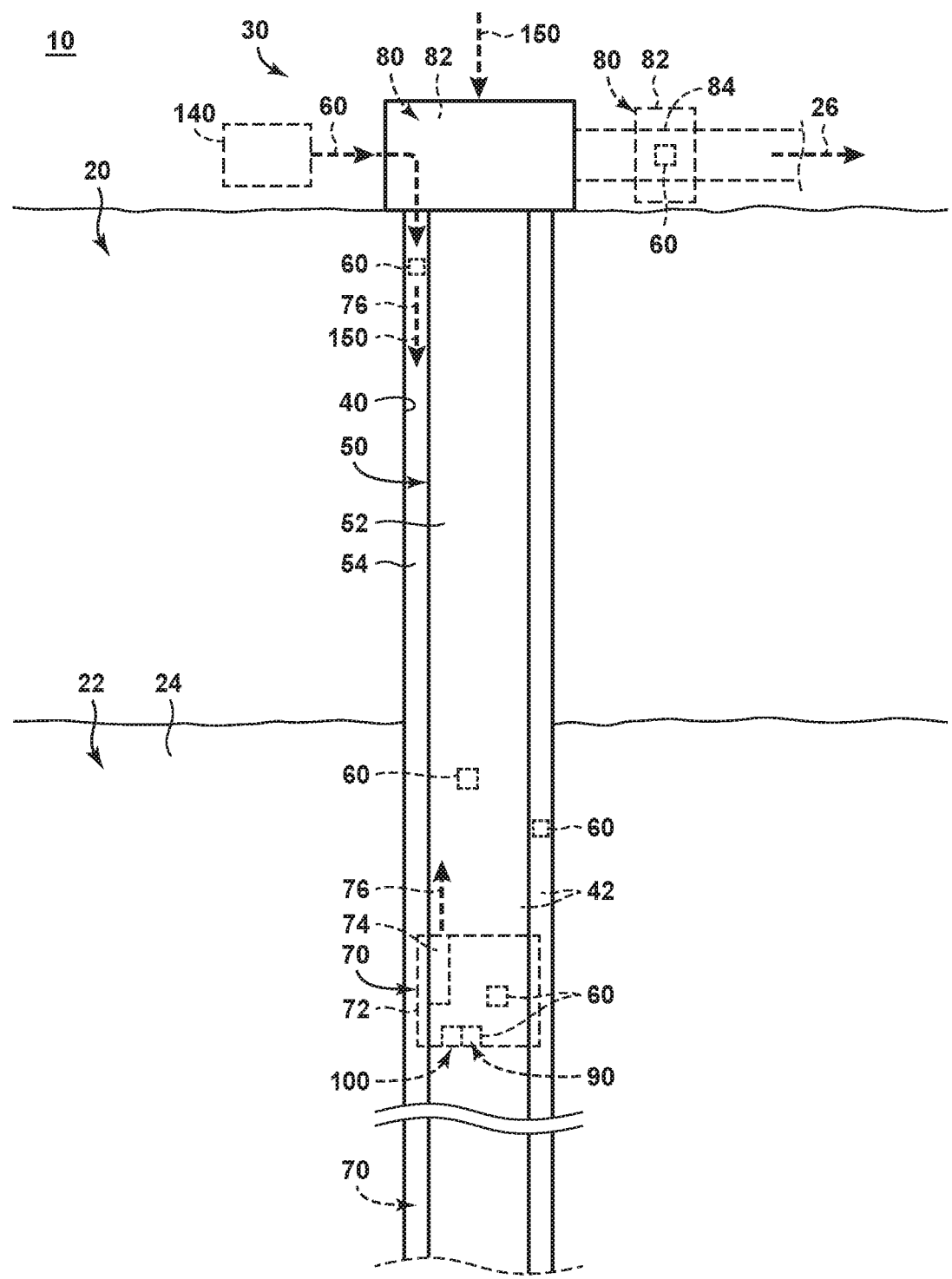
FIG. 1 is a schematic illustration of examples of hydrocarbon wells according to the present disclosure.

FIGS. 1-4 provide examples of hydrocarbon wells 30 and/or methods 200, according to the present disclosure. Elements that serve a similar, or at least substantially similar, purpose are labeled with like numbers in each of FIGS. 1-4, and these elements may not be discussed in detail herein with reference to each of FIGS. 1-4. Similarly, all elements may not be labeled in each of FIGS. 1-4, but reference numerals associated therewith may be utilized herein for consistency. Elements, components, and/or features that are discussed herein with reference to one or more of FIGS. 1-4 may be included in and/or utilized with any of FIGS. 1-4 without departing from the scope of the present disclosure. In general, elements that are likely to be included in a particular embodiment are illustrated in solid lines, while elements that are optional are illustrated in dashed lines. However, elements that are shown in solid lines may not be essential and, in some embodiments, may be omitted without departing from the scope of the present disclosure.

Figure 2:
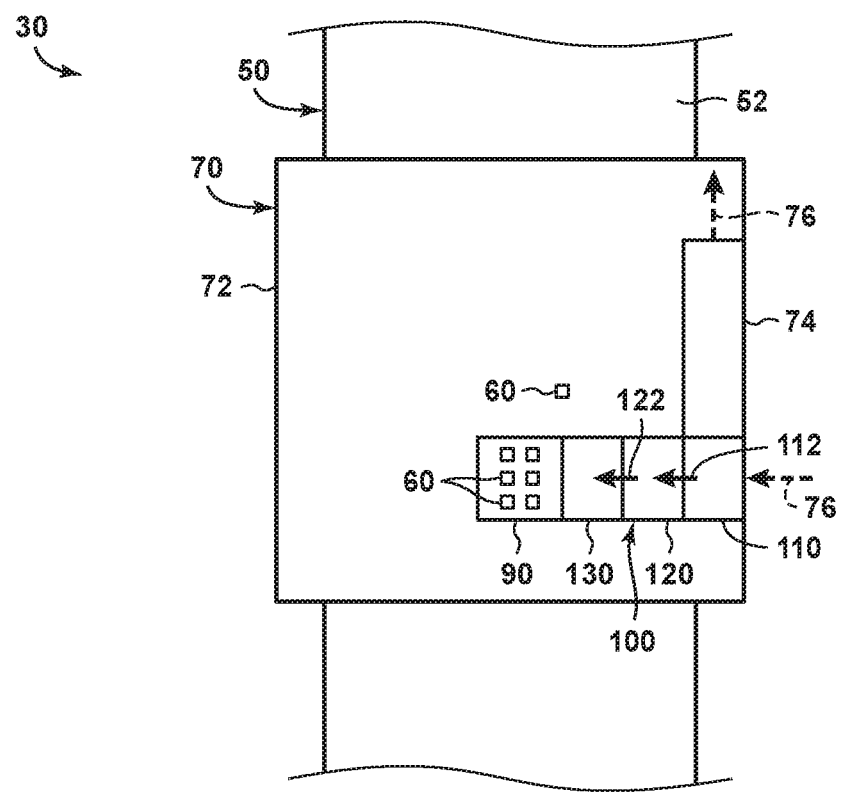
FIG. 2 is a more detailed, but still schematic, illustration of examples of a region of the hydrocarbon wells of FIG. 1.

FIG. 1 is a schematic illustration of examples of hydrocarbon wells 30 according to the present disclosure, and FIG. 2 is a more detailed, but still schematic, illustration of examples of a region of the hydrocarbon wells of FIG. 1. As illustrated in FIG. 1, hydrocarbon wells 30 include a wellbore 40 that extends within a subsurface region 20. Wellbore 40 also may be referred to herein as extending between a surface region 10 and the subsurface region, as extending between the surface region and a subterranean formation 22, and/or as extending within the subterranean formation. Subterranean formation 22 may include hydrocarbons 24, examples of which include hydrocarbon fluids, gaseous hydrocarbons, natural gas, liquid hydrocarbons, and/or crude oil. Hydrocarbon wells 30 also include downhole tubing 50 that defines a tubing conduit 52 and extends within the wellbore. Downhole tubing 50 and wellbore 40 may form, define, and/or at least partially bound an annular space 54 therebetween.

Turning more generally to FIGS. 1-2, hydrocarbon wells 30 also include at least one interrogation device 60. Interrogation device 60 is configured to indicate at least one property of fluid flow within the hydrocarbon well, examples of which are disclosed herein. Hydrocarbon wells 30 further include a downhole location 70 at which interrogation device 60 is released into tubing conduit 52. Wells 30 often may include a plurality of such interrogation devices 60. An interrogation device 60 may be released or a plurality of interrogation devices 60 may be released individually, selectively released or intermittently released in response to a release determination, such as expiration of a time period or displacement interval, a generated release signal, manually or automatically released. Releasing of the interrogation devices 60 into the wellbore for interrogation therein may occur in response to manual or automatic instruction or action, such as in response to occurrence of a downhole event, condition, or activity within the wellbore, or in response to a signal generated from within the wellbore or from the surface. Interrogation devices 60 may be released from a carrier housing or storage structure 90 built into or provided in a wellbore tubular, an inserted or deployed carrier tool conveyed autonomously, on wireline, or coil tubing or jointed tubular string, or deployed from the surface and circulated or flowed downhole via an annulus 54 between tubulars to a subsurface position to for introduction into the well 30 for interrogation therein.

Returning to FIG. 1, hydrocarbon wells 30 may also include a detection structure 80. Detection structure 80 may be configured to query interrogation device 60 to determine the at least one property of fluid flow within the hydrocarbon well.

Figure 4:
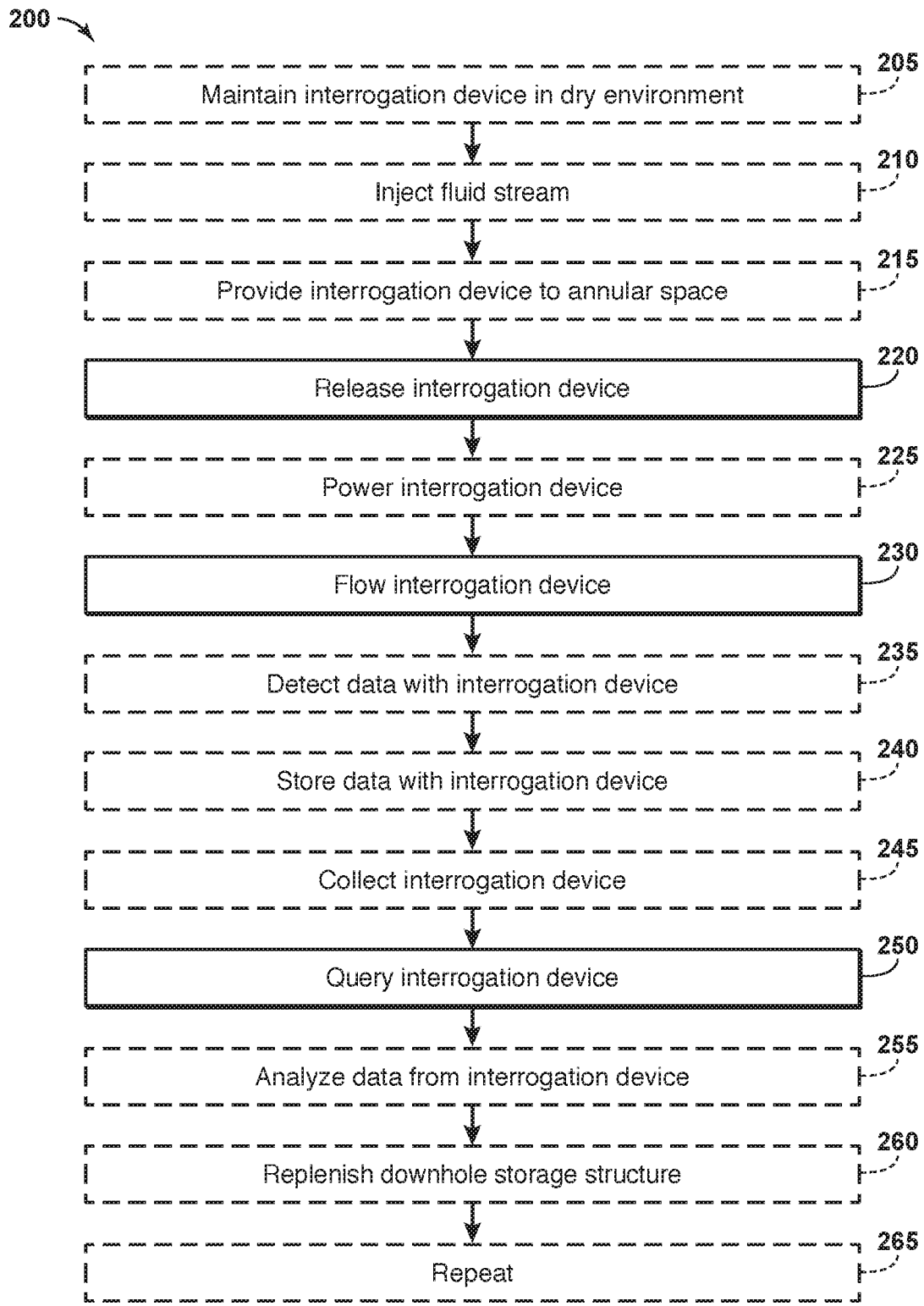
FIG. 4 is a flowchart depicting examples of methods of interrogating fluid flow within a hydrocarbon well, according to the present disclosure.

During operation of hydrocarbon wells 30, and as discussed in more detail herein with reference to the examples of methods 200 of FIG. 4, interrogation device 60, or even a plurality of interrogation devices 60, may be released into tubing conduit 52 at, near, and/or within downhole location 70. This may include release of the interrogation device from a downhole storage structure 90 that may include, house, and/or contain a plurality of interrogation devices 60, as illustrated in dashed lines in FIGS. 1-2. A deployment device or means may also be provided to facilitated deployment of the interrogation devices. Additionally or alternatively, interrogation device 60 may be positioned within annular space 54 and flow, within the annular space, to downhole location 70 before being released into the tubing conduit at the downhole location.

Interrogation device 60 then may flow, within tubing conduit 52, from downhole location 70 to surface region 10. During flow of the interrogation device within the tubing conduit, the interrogation device may detect, measure, and/or determine the at least one property of fluid flow within the hydrocarbon well. The interrogation device then may flow through, past, into contact with, and/or into communicative contact with detection structure 80. The detection structure may query the interrogation device to determine the at least one property of fluid flow within the hydrocarbon well. As an example, the detection structure may receive, from the interrogation device, data, a signal, and/or a data stream, that may be indicative of the at least one property of fluid flow within the hydrocarbon well.

As discussed, and in some examples, interrogation device 60 may be housed within hydrocarbon well 30, such as at, near, and/or within downhole location 70. In these examples, and as also discussed, hydrocarbon well 30 may include downhole storage structure 90, which may include, contain, and/or house one or more interrogation devices 60.

Downhole storage structure 90 may be configured to maintain interrogation device 60 in a dry, or in a liquid-free, environment prior to release of the interrogation device into the tubing conduit. Stated another way, downhole storage structure 90 may be configured to isolate the interrogation device from a wellbore fluid 42 which may extend within the wellbore, prior to release of the interrogation device into the tubing conduit. As an example, downhole storage structure 90 may retain interrogation device 60 between a port seat and a reverse-flow check valve of a gas lift valve 74 that may include, or that may be operatively attached to, the downhole storage structure. Maintaining the interrogation device in the dry environment may decrease a potential for capillary forces between the interrogation device and the downhole storage structure and/or between adjacent interrogation devices that may be positioned within the downhole storage structure. This may increase a reliability and/or repeatability of release 3o of the interrogation device from the downhole storage structure.

As discussed, downhole storage structure 90 may be operatively attached to and/or may form a portion of gas lift valve 74. Examples of downhole structures 72 of hydrocarbon well 30 that may include and/or be operatively attached to the downhole storage structure include a gas lift mandrel, a check valve, a packer, a plug, and/or a chemical injection mandrel.

As also discussed, downhole storage location 90 may include one or more interrogation devices 60. In some examples, the downhole storage location may include a plurality of separate, distinct, and/or independent interrogation devices 60 and/or may be configured to selectively, sequentially, and/or independently release individual ones of the plurality of interrogation devices into the tubing conduit. As examples, the downhole storage location may include at least 10, at least 50, at least 100, at least 250, at least 500, at least 1,000, at least 2,500, at least 5,000, at least 10,000, at most 100,000, at most 75,000, at most 50,000, at most 25,000, at most 10,000, at most 5,000, and/or at most 1,000 interrogation devices 60.

With continued reference to FIGS. 1-2, hydrocarbon well 30 may include a release mechanism 100, which may be configured to release the interrogation device from the downhole storage structure. Examples of release mechanism 100 include an electric release mechanism, an electric actuator, a pump, a hydraulic release mechanism, and/or a mechanical release mechanism.

In some examples, downhole location 70 may include a mandrel that includes gas lift valve 74. Gas lift valve 74 may be configured to inject a lift gas stream 76 into tubing conduit 52. In these examples, and as illustrated in FIG. 2, release mechanism 100 may include a rotary assembly 110, such as a paddle wheel and/or a turbine. Rotary assembly 110 may be configured to rotate responsive to flow of at least a portion of the lift gas stream therepast, thereacross, and/or therethrough. As an example, a slip stream from the lift gas stream may be utilized to rotate the rotary assembly. Rotation of the rotary assembly may produce and/or generate a motive force 112. Stated another way, rotary assembly 110 may generate motive force 112 responsive to flow of the portion of the lift gas stream thereacross.

Release mechanism 100 may be configured to release interrogation device 60 from downhole storage structure 90 responsive to flow of a predetermined volume of the portion of the fluid stream across the rotary assembly. As an example, the release mechanism may include a gear assembly 120, and the rotary assembly may be configured to apply the motive force to the gear assembly. In such an example, the gear assembly may be configured to generate a gear assembly output 122 responsive to receipt of the motive force from the rotary assembly, and the gear assembly output may be utilized to trigger, or to initiate, release of interrogation 3o device 60 after the predetermined volume of the portion of the fluid stream flows across the rotary assembly. As an example, release mechanism 100 may include an interrogation device release structure 130 configured to receive the gear assembly output and to release the interrogation device from the downhole storage structure responsive to receipt of the gear assembly output.

When release mechanism 100 includes rotary assembly 110, gear assembly 120, and interrogation device release structure 130, the release mechanism may be configured to repeated release one or more interrogation devices 60 from downhole storage structure 90 when, whenever, and/or responsive to flow of the predetermined volume of the portion of the fluid stream across the rotary assembly. Stated another way, the release mechanism may release a first interrogation device responsive to a first instance of flow of the predetermined volume of the portion of the fluid stream across the rotary assembly. Release mechanism 100 subsequently may release a second interrogation device responsive to a second instance of flow of the predetermined volume of the portion of the fluid stream across the rotary assembly. This process may be repeated until all interrogation devices 60 contained within, or configured to be released from, downhole storage structure 90 have been released from the downhole storage structure.

As also discussed, and in some examples, interrogation device 60 may be housed within, or near, surface region 10. In these examples, and as also discussed, the interrogation device may be provided to, or may flow to, downhole location 70 within annular space 54, as illustrated in FIG. 1. As an example, hydrocarbon well 30 may include a pressurized container 140 that may house, contain, and/or include one or more interrogation devices 60 and/or may be positioned within surface region 10. In this example, pressurized container 140 may provide interrogation device 60 to annular space 54. The interrogation device then may flow, within the annular space and/or within an injected fluid stream 150 that also may be provided to the annular space, to downhole location 70 before being injected into tubing conduit 52 at the downhole location. Examples of the injected fluid stream include lift gas stream 76.

Detection structure 80 may include any suitable structure that may be adapted, configured, designed, and/or constructed to query interrogation device 60 and/or to determine the at least one property of fluid flow within the hydrocarbon well from interrogation device 60. As an example, detection structure 80 may be configured to query the interrogation device as the interrogation device flows past the detection structure in and/or within a produced fluid stream 26 that is produced from the hydrocarbon well. In this example, hydrocarbon well 30 and/or detection structure 80 may include a region, or a section, of specialized pipe 84 that may be selected to improve a sensitivity of detection of interrogation device 60 by detection structure 80.

As another example, detection structure 80 may include a collection structure 82. Collection structure 82 may be configured to separate interrogation device 60 from the produced fluid stream and/or to collect one or more interrogation devices 60. Detection structure 80 may be configured to determine the at least one property of fluid flow within the hydrocarbon well subsequent to separation of the interrogation device from the produced fluid stream by the collection structure and/or subsequent to collection of the interrogation device within the collection structure. Examples of collection structure 82 include a screen, a filter, and/or a magnetic assembly. When collection structure 82 includes a magnetic assembly, interrogation device 60 may include a magnetically active material, such as a ferromagnetic material, that may be attracted to the magnetic assembly.

It is within the scope of the present disclosure that detection structure 80 may be configured to query interrogation device 60 in any suitable manner. As an example, and as discussed in more detail herein, interrogation device 60 may include an optical identification device. In this example, detection structure 80 may be configured to detect an optical identifier of the optical identification device. As another example, and as also discussed in more detail herein, interrogation device 60 may include a radio frequency identification device. In this example, detection structure 80 may be configured to detect a radio frequency identifier of the radio frequency identification device. As yet another example, and as also discussed in more detail herein, interrogation device 60 may include a data transmitter configured to transmit a wireless data communication. In this example, detection structure 80 may be configured to detect the wireless data communication from the data transmitter.

Detection structure 80 may be positioned within any suitable portion, or region, of the hydrocarbon well. As an example, and as illustrated in FIG. 1, interrogation device 80 may be positioned within surface region 10.

Downhole location 70 may include and/or be any suitable structure that may be configured to release, or to permit release of, interrogation device 60 into tubing conduit 52. Examples of the downhole location include the gas lift mandrel, the gas lift valve, the check valve, the packer, the plug, and/or the chemical injection mandrel.

Figure 3:
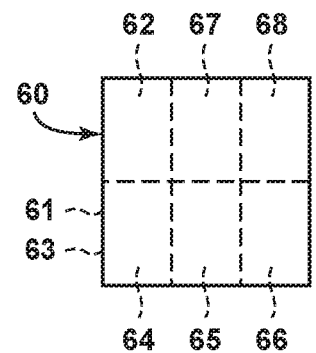
FIG. 3 is a schematic illustration of examples of an interrogation device that may be utilized with the hydrocarbon wells and/or methods, according to the present disclosure.

FIG. 3 is a schematic illustration of examples of an interrogation device 60 that may be utilized with the hydrocarbon wells 30 of FIGS. 1-2 and/or with methods 200 of FIG. 4, according to the present disclosure. In some examples, interrogation device 60 may include and/or be a passive interrogation device 61. Examples of passive interrogation devices 61 include radio frequency identification devices and/or optical identification devices. Passive interrogation devices 61 may have, include, and/or define a unique identifier 62 that may be associated with the passive interrogation device.

The unique identifier may be specific to a given passive interrogation device. Stated another way, and when hydrocarbon wells 30 include the plurality of interrogation devices 60, each interrogation device of the plurality of interrogation devices may include a different, a distinct, and/or a corresponding unique identifier that may uniquely distinguish a given interrogation device from each other interrogation device. In such a configuration, the at least one property of fluid flow within the hydrocarbon well may be determined based, at least in part, on a time period between release of a given interrogation device into the hydrocarbon well and detection of the given interrogation device by the detection structure. As an example, and with reference to FIG. 1, a given interrogation device 60 may be conveyed within annular space 54 to downhole location 70 and released into tubing conduit 52 at the downhole location. In this example, an identity of downhole location 70 and/or a depth of downhole location 70 within the hydrocarbon well may be determined based, at least in part, on the time period.

Additionally or alternatively, and when hydrocarbon well 30 includes downhole storage structure 90, the unique identifier may be specific to a given downhole location 70. Stated another way, hydrocarbon well 30 may include a plurality of downhole locations 70, and the unique identifier may associate a given interrogation device 60 with a given downhole location 70. In this example, and as discussed, interrogation devices 60 may be released from a given downhole location 70 based, at least in part, on flow of lift gas stream 76 through a gas lift valve 74 that is associated with the given downhole location. Thus, detection of the given interrogation device by detection structure 80 may indicate that the lift gas stream is flowing through the lift gas valve that is associated with the given downhole location.

Stated another way, the at least one property of fluid flow within the hydrocarbon well may include identification which gas lift valve(s) is/are injecting the lift gas stream at a given point in time.

Returning to FIG. 3, in some examples, interrogation device 60 may include and/or be an active interrogation device 63. Active interrogation devices 63 may be electrically powered and/or may be configured to actively interrogate and/or determine the at least one property of fluid flow within the hydrocarbon well. Such electrically powered active interrogation devices 63 may include an energy storage device 65 that may be configured to electrically power the active interrogation device.

As an example, active interrogation devices 63 may include a sensor 64 configured to detect the at least one property of fluid flow within the hydrocarbon well. Examples of 3o sensor 64 include a temperature sensor configured to detect a temperature of fluid within the hydrocarbon well, a pressure sensor configured to detect a pressure of fluid within the hydrocarbon well, a pH sensor configured to detect a pH of fluid within the hydrocarbon well, a resistivity sensor configured to detect an electrical resistivity of fluid within the hydrocarbon well, a vibration sensor configured to detect vibration within the hydrocarbon well, an acceleration sensor configured to detect an acceleration of the interrogation device as the interrogation device is conveyed within the hydrocarbon well, and/or a velocity sensor configured to detect a velocity of the interrogation device as the interrogation device is conveyed within the hydrocarbon well.

As illustrated in dashed lines in FIG. 3, active interrogation devices 63 may include an initiation structure 66. Initiation structure 66, when present, may be configured to initiate supply of electrical power to a remainder of the active initiation device, or to turn the active initiation device "on," responsive to fluid contact between the active interrogation device and a wellbore fluid. Examples of initiation structure 66 include a fluid-sensitive electrical contact and/or an insulating coating that may be soluble within the wellbore fluid.

As also illustrated in dashed lines in FIG. 3, active interrogation devices 63 may include a memory device 67. Memory device 67, when present, may be configured to store data collected by the active interrogation device, such as when and/or while the active interrogation device is conveyed within the tubing conduit. Examples of memory device 67 include solid state memory devices, volatile memory devices, non-volatile memory devices, and/or flash memory devices.

As also illustrated in dashed lines in FIG. 3, active interrogation devices 63 may include a data transmitter 68. As discussed in more detail herein, data transmitter 68, when present, may be configured to transmit data collected by the active interrogation device and/or stored within memory device 67 to detection structure 80 of FIG. 1. Examples of data transmitter 68 include a wireless data transmitter, a radio frequency data transmitter, and/or a Bluetooth data transmitter.

FIG. 4 is a flowchart depicting examples of methods 200 of interrogating fluid flow within a hydrocarbon well, according to the present disclosure. Methods 200 may include maintaining an interrogation device in a dry environment at 205, injecting a fluid stream at 210, and/or providing the interrogation device to an annular space at 215. Methods 200 include releasing the interrogation device at 220 and may include powering the interrogation device at 225. Methods 200 also include flowing the interrogation device at 230 and may include detecting data with the interrogation device at 235, storing data with the interrogation device at 240, and/or collecting the interrogation device at 245. Methods 200 further include querying the interrogation device at 250 and may include analyzing data from the interrogation device at 255, replenishing a downhole storage structure at 260, and/or repeating at least a portion of the methods at 265.

Maintaining the interrogation device in the dry environment at 205 may include maintaining the interrogation device in the dry, or liquid-free, environment prior to the releasing. This may include fluidly isolating the interrogation device from a wellbore fluid that extends within the wellbore and/or otherwise restricting fluid contact between the interrogation device and liquid. The maintaining at 205 may permit, facilitate, and/or improve the releasing at 220, as discussed in more detail herein. Examples of the interrogation device are disclosed herein with reference to interrogation device 60 of FIGS. 1-3.

The maintaining at 205 may be accomplished in any suitable manner. As an example, the maintaining at 205 may include maintaining the dry environment within a pressurized container that is positioned within a surface region. Examples of the pressurized container are disclosed herein with reference to pressurized container 140 of FIG. 1. As another example, the maintaining at 205 may include maintaining the dry environment within a downhole storage structure that may be positioned at, near, and/or within a downhole location at which the releasing at 220 may be performed. Examples of the downhole storage structure are disclosed herein with reference to downhole storage structure 90 of FIGS. 1-2.

The releasing at 220 may include releasing the interrogation device at the downhole location. In some examples, the downhole location may include, or be, a gas lift valve. Under these conditions, methods 200 may include the injecting at 210. The injecting at 210 may include injecting an injected fluid stream, such as a lift gas stream, through the gas lift valve and/or into a tubing conduit defined by downhole tubing that extends within a wellbore of the hydrocarbon well. This may include injecting to provide artificial lift for the hydrocarbon well.

Examples of the downhole location are disclosed herein with reference to downhole location 70 of FIGS. 1-2. Examples of the gas lift valve are disclosed herein with reference to gas lift valve 74 of FIGS. 1-2. Examples of the downhole tubing are disclosed herein with reference to downhole tubing 50 of FIG. 1.

As discussed, and in some examples, the interrogation device may be stored, housed, and/or maintained at and/or within the surface region, such as within the pressurized container. In these examples, methods 200 may include providing the interrogation device to the annular space at 215, such as from the pressurized container and/or via an injection port and/or a needle valve that may extend between the pressurized container and the annular space. The providing at 215 additionally or alternatively may include flowing the interrogation device within the annular space to the downhole location within the injected fluid stream. In these examples, the releasing at 220 may include injecting the interrogation device into the tubing conduit with and/or within the injected fluid stream.

The annular space may extend between the downhole tubing and the wellbore. Examples of the annular space are disclosed herein with reference to annular space 54 of FIG. 1.

Releasing the interrogation device at 220 may include releasing the interrogation device at the downhole location and/or within the hydrocarbon well. In some examples, and as discussed, the downhole location may include a mandrel that includes a gas lift valve. In these examples, the releasing at 220 may include releasing responsive to, or as a result of, fluid flow through the gas lift valve. In these examples, the at least one property of fluid flow within the hydrocarbon well may include an identity of the gas lift valve through which the fluid flows.

In some examples, and as discussed, the injecting at 210 and/or the providing at 215 may be performed to produce, to generate, and/or to facilitate the releasing at 220. As an example, the providing at 215 may be performed to convey the interrogation device to the downhole location, and the interrogation device may be released into the tubing conduit at the downhole location as part of, or responsive to, the injecting at 210. As an example, the releasing at 220 may include releasing the interrogation device into and/or within the injected fluid stream.

In other examples, and as discussed, the hydrocarbon well and/or the mandrel may include the downhole storage structure, which may house and/or contain one or more interrogation devices. In these examples, the releasing at 220 may include releasing the interrogation device from the downhole storage structure. The downhole storage structure also may be referred to herein as a downhole storage location, a downhole storage volume, and/or a downhole storage container. Examples of the downhole storage structure and/or of downhole components that may include the downhole storage structure include a gas lift mandrel, a gas lift valve, a check valve, a packer, a plug, and/or a chemical injection mandrel.

It is within the scope of the present disclosure that the releasing at 220 may include releasing with, via, and/or utilizing a release mechanism. Examples of the release mechanism are disclosed herein with reference to release mechanism 100 of FIGS. 1-2.

In some examples, and as discussed, the releasing at 220 may include releasing with, within, and/or into an injected fluid stream, such as the injected fluid stream that is injected during the injecting at 210. In these examples, methods 200 further may include powering the release mechanism with the injected fluid stream.

As an example, the release mechanism may include a rotary assembly. In this example, methods 200 may include flowing at least a portion of the injected fluid stream, such as a slip stream of the injected fluid stream, through and/or across the rotary assembly and generating a motive force with the rotary assembly responsive thereto. The release mechanism further may include a gear assembly, and methods 200 may include applying the motive force to the gear assembly and generating a gear assembly output responsive thereto. The release mechanism also may include an interrogation device release structure, and methods 200 may include applying the gear assembly output to the interrogation device release structure, and the releasing at 220 may include releasing the interrogation device from the downhole storage structure with the release structure responsive to receipt of the gear assembly output by the interrogation device release structure. The rotary assembly and/or the gear assembly may be configured such that the interrogation device is released responsive to flow of a predetermined volume of the portion of the injected fluid stream across the rotary assembly.

Examples of the rotary assembly are disclosed herein with reference to rotary assembly 110 of FIG. 2. Examples of the gear assembly are disclosed herein with reference to gear assembly 120 of FIG. 2. Examples of the interrogation device release structure are disclosed herein with reference to interrogation device release structure 130 of FIG. 2.

In some examples, and as discussed, the interrogation device may include and/or be an active interrogation device. As also discussed, the active interrogation device may include and/or be an electrically powered active interrogation device. In these examples, methods 200 further may include powering the interrogation device at 225.

The powering at 225 may be accomplished in any suitable manner. As an example, the interrogation device may include an energy storage device, such as a battery and/or a capacitor. In this example, the powering at 225 may include powering the interrogation device with, via, and/or utilizing the energy storage device.

When methods 200 include the powering at 225, the powering at 225 may be initiated based upon and/or responsive to any suitable condition and/or criteria. As an example, the powering at 225 may be initiated responsive to fluid contact between the interrogation device and the wellbore fluid. Such a configuration may permit the interrogation device to remain in a dormant, or power-conserving, state prior to contact with the wellbore fluid and/or may permit the interrogation device to transition to an active, or power-consuming, state upon, or responsive to, contact with the wellbore fluid.

In some examples, the powering of the interrogation device may occur instantly, or at least substantially instantly, upon contact with the wellbore fluid. In other examples, the interrogation device may be configured such that the powering is delayed for a predetermined delay time period subsequent to contact with the wellbore fluid.

Flowing the interrogation device at 230 may include flowing the interrogation device from the downhole location and/or to the surface region. This may include flowing with, within, and/or via the tubing conduit. The flowing at 230 may be accomplished in any suitable manner. As an example, the flowing at 230 may include flowing the interrogation device within produced fluid, or within a produced fluid stream, that is produced from the hydrocarbon well. As another example, the flowing at 230 may include flowing during, as part of, and/or responsive to an artificial lift operation within the hydrocarbon well.

Detecting data with the interrogation device at 235 may include detecting data, or information, regarding the hydrocarbon well, regarding the wellbore fluid, and/or regarding fluid flow within the hydrocarbon well with, via, and/or utilizing the interrogation device. As an example, and when the interrogation device includes the active interrogation device, the active interrogation device may include a sensor. The sensor may be configured to detect the information regarding the hydrocarbon well, the information regarding the wellbore fluid, and/or the information regarding fluid flow within the hydrocarbon well. The sensor additionally or alternatively may be configured to detect the at least one property of fluid flow within the hydrocarbon well and/or to collect data that is indicative of the at least one property of fluid flow within the hydrocarbon well. When methods 200 include the detecting at 235, the querying at 250 may include receiving sensor data from the active interrogation device.

In some examples, the sensor may include a temperature sensor. In these examples, the detecting at 235 may include detecting temperature data. As a more specific example, the detecting at 235 may include detecting a temperature profile between the downhole location and the surface region. When the sensor includes the temperature sensor, the querying at 250 may include receiving the temperature data and/or the temperature profile from the active interrogation device.

In these examples, the analyzing at 255 may include analyzing the temperature data and/or the temperature profile data to determine one or more locations, between the downhole location and the surface region, where lift gas is being injected into the tubing conduit. This may be accomplished, for example, by measuring temperature fluctuations within the tubing conduit and correlating these temperature fluctuations to locations where the lift gas is being injected. More specifically, injection of the lift gas may cause a cooling effect, such as via the Joule-Thompson Effect. As such, detection of a temperature decrease at a specific location may indicate lift gas injection at that specific location.

In these examples, the analyzing at 250 additionally or alternatively may include analyzing the temperature data and/or the temperature profile data to determine, to estimate, and/or to calculate a volume of lift gas that is being injected at each of the locations where lift gas is being injected into the tubing conduit. As an example, a magnitude of the temperature fluctuation, or of the temperature decrease, at the specific location may be indicative of the volume of lift gas injected at that specific location.

In some examples, the sensor may include a pressure sensor. In these examples, the detecting at 235 may include detecting pressure data. As a more specific example, the detecting at 235 may include detecting a pressure profile between the downhole location and the surface region. When the sensor includes the pressure sensor, the querying at 250 may include receiving the pressure data and/or the pressure profile from the active interrogation device.

In these examples, the analyzing at 255 may include analyzing the pressure data and/or the pressure profile data to determine one or more locations, between the downhole location and the surface region, where lift gas is being injected into the tubing conduit. This may be accomplished, for example, by measuring pressure fluctuations within the tubing conduit and correlating these pressure fluctuations to locations where the lift gas is being injected. More specifically, injection of the lift gas may cause localized pressure variations. As such, detection of these localized pressure variations may indicate lift gas injection at specific locations.

In these examples, the analyzing at 250 additionally or alternatively may include analyzing the pressure data and/or the pressure profile data to determine, to estimate, and/or to calculate a volume of lift gas that is being injected at each of the locations where lift gas is being injected into the tubing conduit. As an example, a magnitude of the localized pressure fluctuations at a specific location may be indicative of the volume of lift gas injected at that specific location.

In some examples, the sensor may include a pH sensor. In these examples, the detecting at 235 may include detecting pH data. As a more specific example, the detecting at 235 may include detecting a pH profile between the downhole location and the surface region. When the sensor includes the pH sensor, the querying at 250 may include receiving the pH data and/or the pH profile from the active interrogation device.

In these examples, the analyzing at 255 may include analyzing the pH data and/or the pH profile data to determine one or more locations, between the downhole location and the surface region, where lift gas is being injected into the tubing conduit. This may be accomplished, for example, by including a pH-modifying component, such as carbon dioxide, within the lift gas. Injection of the pH-modifying component may cause changes in the pH of the wellbore fluid, which may be detected by the pH sensor. As such, detection of localized pH fluctuations may indicate lift gas injection at specific locations.

In these examples, the analyzing at 250 additionally or alternatively may include analyzing the pH data and/or the pH profile data to determine, to estimate, and/or to calculate a volume of lift gas that is being injected at each of the locations where lift gas is being injected into the tubing conduit. As an example, a magnitude of the localized pH fluctuations at a specific location may be indicative of the volume of lift gas injected at that specific location.

In some examples, the sensor may include a resistivity sensor. In these examples, the detecting at 235 may be detecting resistivity data, or a resistivity profile, between the downhole location and the surface region, and the querying at 250 may include receiving the resistivity data and/or the resistivity profile from the active interrogation device.

In some examples, the sensor may include a vibration sensor. In these examples, the detecting at 235 may be detecting vibration data, or a vibration profile, between the downhole location and the surface region, and the querying at 250 may include receiving the vibration data and/or the vibration profile from the active interrogation device.

In some examples, the sensor may include an acceleration sensor. In these examples, the detecting at 235 may include detecting acceleration data, or an acceleration profile, between the downhole location and the surface region, and the querying at 250 may include receiving the acceleration data and/or the acceleration profile from the active interrogation device.

In some examples, the sensor may include a velocity sensor. In these examples, the detecting at 235 may include detecting velocity data, or a velocity profile, between the downhole location and the surface region, and the querying at 250 may include receiving the velocity data and/or the velocity profile from the active interrogation device.

Storing data with the interrogation device at 240 may include storing any suitable data with and/or utilizing any memory device of the interrogation device. Examples of the data include the temperature data, the temperature profile, the pressure data, the pressure profile, the pH data, the pH profile, the resistivity data, the resistivity profile, the vibration data, the vibration profile, the acceleration data, the acceleration profile, the velocity data, and/or the velocity profile. Examples of the memory device are disclosed herein with reference to memory device 67 of FIG. 3. When methods 200 include the storing at 240, the querying at 250 may include retrieving the data from the memory device and/or transmitting the data from the memory device to the detection structure.

Collecting the interrogation device at 245 may include collecting the interrogation device with, via, and/or utilizing any suitable collection structure. This may include collecting to produce and/or facilitate the querying at 250. Examples of the collection structure are disclosed herein with reference to collection structure 82 of FIG. 1.

When methods 200 include the collecting at 245, the querying at 250 may be subsequent and/or responsive to the collecting at 245. As an example, and as discussed herein with reference to FIG. 1, the interrogation device may be removed from the produced fluid stream and/or collected with the collection device and subsequently may be queried by the detection structure. This may provide additional time for the detection structure to receive data from the interrogation device when compared to examples in which the detection structure might query the interrogation device as the interrogation device flows past the detection structure within the produced fluid stream.

Querying the interrogation device at 250 may include querying the interrogation device to determine the at least one property of fluid flow within the hydrocarbon well. This may include querying within the surface region, querying during the flowing at 230, and/or querying subsequent to the collecting at 245.

In some examples, and as discussed, the interrogation device may include and/or be a passive interrogation device, examples of which are disclosed herein. As also discussed, the passive interrogation device may include a unique identifier that may be associated with the passive interrogation device and/or that may associate the passive interrogation device with the downhole location. Under these conditions, the querying at 250 may include detecting the unique identifier. Additionally or alternatively, the at least one property of fluid flow within the hydrocarbon well may include and/or be an identity of the downhole location, which may be established based, at least in part, on the unique identifier.

In some examples, and as discussed, the interrogation device may include and/or be an active interrogation device, examples of which are disclosed herein. In these examples, the querying at 250 may include receiving a data stream from the active interrogation device. As a more specific example, the active interrogation device may include a data transmitter, and methods 200 may include transmitting data collected by the active interrogation device, as the data stream, during the querying at 250. In this example, the querying at 250 further may include receiving the data collected by the active interrogation device, such as with, via, and/or utilizing the detection structure. Examples of the data transmitter are disclosed herein with reference to data transmitter 68 of FIG. 3.

Analyzing data from the interrogation device at 255 may include analyzing the data to determine, to calculate, to estimate, and/or to establish the at least one property of fluid flow within the hydrocarbon well. Examples of the analyzing at 255 are disclosed herein.

As discussed, hydrocarbon wells according to the present disclosure may include a downhole storage structure that may include, contain, and/or house a plurality of interrogation devices. In these examples, and as discussed in more detail herein, methods 200 may be repeated a plurality of times to release the plurality of interrogation devices at the downhole location. As such, the downhole storage structure eventually may be depleted of interrogation devices.

In some examples, at least one interrogation device of the plurality of interrogation devices may include a quantity identifier. The quantity identifier may indicate when fewer than a threshold number of interrogation devices remain within the downhole storage structure. The releasing at 220 may include releasing the at least one interrogation device that includes the quantity identifier, and the querying at 250 may include detecting the quantity identifier.

When the downhole storage structure is depleted of interrogation devices, when the downhole storage structure includes less than the threshold number of interrogation devices, when the quantity identifier is detected during the querying at 250, and/or for any other suitable reason, methods 200 may include replenishing the downhole storage structure at 260. The replenishing at 260 may include replenishing the downhole storage structure with a plurality of new interrogation devices. As an example, the replenishing at 260 may include retrieving the downhole storage structure from the downhole location and returning a replenished downhole storage structure, which includes the plurality of new interrogation devices, to the downhole location.

Repeating at least the portion of the methods at 265 may include repeating any suitable portion of methods 200 in any suitable order and/or sequence. As an example, the interrogation device may be a first interrogation device and the hydrocarbon well may include the downhole storage structure that includes the plurality of interrogation devices. Under these conditions, the repeating at 265 may include repeating, periodically repeating, intermittently repeating, sequentially repeating, and/or continuously performing one or more of the maintaining at 205, the injecting at 210, the providing at 215, the releasing at 220, the powering at 225, the flowing at 230, the detecting at 235, the storing at 240, the collecting at 245, the querying at 250, the analyzing at 255, and/or the replenishing at 260. As a more specific example, the repeating at 265 may include repeating the releasing at 220, the flowing at 230, and the querying at 250 with a given, or with each, interrogation device of the plurality of interrogation devices. This may include repeating the releasing at 220, the flowing at 230, and the querying at 250 to release a plurality of corresponding interrogation devices, to flow the plurality of corresponding interrogation devices from the downhole location to the surface region, and/or to query the plurality of corresponding interrogation devices, such as to determine a plurality of corresponding properties of fluid flow within the hydrocarbon well.

It is within the scope of the present disclosure that the repeating at 265 may include repeating responsive to release criteria. Examples of the release criteria include a user indication, expiration of a predetermined time interval, flow of a predetermined volume of produced fluid produced by the hydrocarbon well, flow of a predetermined volume of injected fluid injected into the hydrocarbon well, and/or measurement of a pressure within the hydrocarbon well. The repeating at 265 may be performed and/or initiated manually. Additionally or alternatively, a controller may be utilized to regulate the repeating at 265.

In the present disclosure, several of the illustrative, non-exclusive examples have been discussed and/or presented in the context of flow diagrams, or flow charts, in which the methods are shown and described as a series of blocks, or steps. Unless specifically set forth in the accompanying description, it is within the scope of the present disclosure that the order of the blocks may vary from the illustrated order in the flow diagram, including with two or more of the blocks (or steps) occurring in a different order and/or concurrently.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B," when used in conjunction with open-ended language such as "comprising" may refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

As used herein, the phrase "at least one," in reference to a list of one or more entities should be understood to mean at least one entity selected from any one or more of the entities in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C," and "A, B, and/or C" may mean A alone, B alone, C alone, A and B together, A and C together, B and C together, A, B, and C together, and optionally any of the above in combination with at least one other entity.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

As used herein the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa.

As used herein, the phrase, "for example," the phrase, "as an example," and/or simply the term "example," when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, "at least substantially," when modifying a degree or relationship, may include not only the recited "substantial" degree or relationship, but also the full extent of the recited degree or relationship. A substantial amount of a recited degree or relationship may include at least 75% of the recited degree or relationship. For example, an object that is at least substantially formed from a material includes objects for which at least 75% of the objects are formed from the material and also includes objects that are completely formed from the material. As another example, a first length that is at least substantially as long as a second length includes first lengths that are within 75% of the second length and also includes first lengths that are as long as the second length. As yet another example, elements that are at least substantially parallel includes elements that extend in directions that deviate by up to 22.5° and also includes elements that are parallel.

INDUSTRIAL APPLICABILITY

The systems and methods disclosed herein are applicable to the oil and gas industries.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions, and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements, and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:

1. A method of interrogating fluid flow within a hydrocarbon well, the method comprising:
   releasing an interrogation device at a downhole location within the hydrocarbon well;
   flowing the interrogation device from the downhole location to a surface region via a tubing conduit defined by downhole tubing that extends within a wellbore of the hydrocarbon well; and
   querying the interrogation device to determine at least one property of fluid flow within the hydrocarbon well;
   wherein the interrogation device includes an active interrogation device, wherein the active interrogation device is an electrically powered active interrogation device, and further wherein the querying includes receiving a data stream from the active interrogation device;

wherein the active interrogation device includes a sensor configured to detect the at least one property of fluid flow within the hydrocarbon well, and further wherein the querying includes receiving sensor data from the active interrogation device; and wherein the sensor includes a temperature sensor, wherein the method includes detecting a temperature profile between the downhole location and the surface region, wherein the querying includes receiving the temperature profile from the active interrogation device, and further wherein the method includes analyzing the temperature profile to determine injection locations, between the downhole location and the surface region, where lift gas is injected into the tubing conduit.

2. The method of claim 1, wherein the downhole location includes a mandrel that includes a gas lift valve, wherein the releasing includes releasing responsive to fluid flow through the gas lift valve, and further wherein the at least one property of fluid flow within the hydrocarbon well includes an identity of the gas lift valve through which the fluid flows.

3. The method of claim 2, wherein the mandrel includes a downhole storage structure for the interrogation device, and further wherein the releasing includes releasing the interrogation device from the downhole storage structure.

4. The method of claim 2, wherein the method further includes injecting the fluid flow through the gas lift valve and into the tubing conduit to provide artificial lift for the hydrocarbon well.

5. The method of claim 1, wherein the interrogation device includes a passive interrogation device that includes a unique identifier that associates the passive interrogation device with the downhole location, and further wherein the querying includes detecting the unique identifier.

6. The method of claim 1, wherein the hydrocarbon well includes a downhole storage structure that stores the interrogation device, and further wherein the releasing includes releasing from the downhole storage structure.

7. The method of claim 6, wherein the interrogation device is a first interrogation device, wherein the downhole storage structure includes a plurality of interrogation devices, and further wherein the method includes periodically repeating the releasing, the flowing, and the querying with a given interrogation device of the plurality of interrogation devices.

8. The method of claim 7, wherein at least one interrogation device of the plurality of interrogation devices includes a quantity identifier that indicates when fewer than a threshold number of interrogation devices remain within the downhole storage structure, and wherein the querying includes detecting the quantity identifier.

9. The method of claim 8, further wherein the method includes replenishing the downhole storage structure with a plurality of new interrogation devices responsive to the detecting the quantity identifier.

10. The method of claim 1, wherein the method further includes providing the interrogation device to an annular space that extends between the downhole tubing and the wellbore and flowing the interrogation device within the annular space to the downhole location within an injected fluid stream, wherein the releasing includes injecting the interrogation device into the tubing conduit within the injected fluid stream.

11. The method of claim 1, wherein the method further includes repeating the releasing, the flowing, and the querying a plurality of times to release a plurality of corresponding interrogation devices at the downhole location, flow the plurality of corresponding interrogation devices from the downhole location to the surface region, and query the plurality of corresponding interrogation devices to determine a plurality of corresponding properties of fluid flow within the hydrocarbon well.

12. The method of claim 1, wherein the querying includes querying during the flowing.

13. The method of claim 1, wherein the method further includes collecting the interrogation device, and further wherein the querying is subsequent to the collecting.

14. The method of claim 1, wherein the hydrocarbon well includes a plurality of gas lift valves, wherein each gas lift valve of the plurality of gas lift valves is configured to inject a corresponding lift gas stream into the tubing conduit, and further wherein the querying includes determining which of the plurality of gas lift valves is injecting the corresponding lift gas stream into the tubing conduit.

15. A method of interrogating fluid flow within a hydrocarbon well, the method comprising:

releasing an interrogation device at a downhole location within the hydrocarbon well;

flowing the interrogation device from the downhole location to a surface region via a tubing conduit defined by downhole tubing that extends within a wellbore of the hydrocarbon well; and querying the interrogation device to determine at least one property of fluid flow within the hydrocarbon well;

wherein the interrogation device includes an active interrogation device, wherein the active interrogation device is an electrically powered active interrogation device, and further wherein the querying includes receiving a data stream from the active interrogation device;

wherein the active interrogation device includes a sensor configured to detect the at least one property of fluid flow within the hydrocarbon well, and further wherein the querying includes receiving sensor data from the active interrogation device; and wherein the sensor includes a pressure sensor, wherein the method includes detecting a pressure profile between the downhole location and the surface region, wherein the querying includes receiving the pressure profile from the active interrogation device, and further wherein the method includes analyzing the pressure profile to determine injection locations, between the downhole location and the surface region, where lift gas is injected into the tubing conduit.

16. A method of interrogating fluid flow within a hydrocarbon well, the method comprising:

releasing an interrogation device at a downhole location within the hydrocarbon well;

flowing the interrogation device from the downhole location to a surface region via a tubing conduit defined by downhole tubing that extends within a wellbore of the hydrocarbon well; and querying the interrogation device to determine at least one property of fluid flow within the hydrocarbon well;

wherein the interrogation device includes an active interrogation device, wherein the active interrogation device is an electrically powered active interrogation device, and further wherein the querying includes receiving a data stream from the active interrogation device;

wherein the active interrogation device includes a sensor configured to detect the at least one property of fluid flow within the hydrocarbon well, and further wherein the querying includes receiving sensor data from the active interrogation device; and wherein the sensor includes a pH sensor, wherein the method includes detecting a pH profile between the downhole location and the surface region, wherein the querying includes receiving the pH profile from the active interrogation device, and further wherein the method includes analyzing the pH profile to determine injection locations, between the downhole location and the surface region, where lift gas is injected into the tubing conduit.

17. A method of interrogating fluid flow within a hydrocarbon well, the method comprising:

releasing an interrogation device at a downhole location within the hydrocarbon well;

flowing the interrogation device from the downhole location to a surface region via a tubing conduit defined by downhole tubing that extends within a wellbore of the hydrocarbon well; and querying the interrogation device to determine at least one property of fluid flow within the hydrocarbon well;

wherein the interrogation device includes an active interrogation device, wherein the active interrogation device is an electrically powered active interrogation device, and further wherein the querying includes receiving a data stream from the active interrogation device;

wherein the active interrogation device includes a sensor configured to detect the at least one property of fluid flow within the hydrocarbon well, and further wherein the querying includes receiving sensor data from the active interrogation device; and wherein the sensor includes at least one of:

(i) a resistivity sensor, wherein the method includes detecting a resistivity profile between the downhole location and the surface region, and further wherein the querying includes receiving the resistivity profile from the active interrogation device;

(ii) a vibration sensor, wherein the method includes detecting a vibration profile between the downhole location and the surface region, and further wherein the querying includes receiving the vibration profile from the active interrogation device;

(iii) an acceleration sensor, wherein the method includes detecting acceleration of the interrogation device during the flowing, and further wherein the querying includes receiving acceleration data from the active interrogation device; and (iv) a velocity sensor, wherein the method includes detecting a velocity of the interrogation device during the flowing, and further wherein the querying includes receiving velocity data from the active interrogation device.

* * * * *